United States Patent [19]
Wagner

[11] Patent Number: 5,883,281
[45] Date of Patent: Mar. 16, 1999

[54] OXYGEN ADDITION TO REDUCE INERTS IN AN ACRYLONITRILE REACTOR

[75] Inventor: Mathew Lincoln Wagner, White Plains, N.Y.

[73] Assignee: Praxair Technology, Inc., Danbury, Conn.

[21] Appl. No.: 898,856

[22] Filed: Jul. 25, 1997

[51] Int. Cl.⁶ ................................................. C07C 253/00
[52] U.S. Cl. .............................................................. 558/320
[58] Field of Search ............................................. 558/320

[56] References Cited

U.S. PATENT DOCUMENTS

| | | | |
|---|---|---|---|
| 4,849,537 | 7/1989 | Ramachandran et al. | 558/319 |
| 4,870,201 | 9/1989 | Ramachandran et al. | 558/319 |
| 5,015,756 | 5/1991 | Ramachandran et al. | 558/320 |
| 5,457,223 | 10/1995 | Shaw et al. | 558/319 |
| 5,466,857 | 11/1995 | Reiling et al. | 558/319 |

FOREIGN PATENT DOCUMENTS 61-13700 of 1986 Japan .

Primary Examiner—Johann Richter
Assistant Examiner—Joseph Murray
Attorney, Agent, or Firm—Bernard Lau

[57] ABSTRACT

A process for increasing the yield of an ammoxidation product by passing a feed into a reactor, passing an oxygen-containing gas stream containing at least a portion of inerts into the reactor, passing a substantially pure oxygen stream into the reactor, and reducing the flow of the oxygen-containing gas stream while increasing the flow of said substantially pure oxygen stream, wherein the total rate of flow of oxygen from the oxygen-containing gas stream and the substantially pure oxygen stream is maintained in an effective amount to produce the ammoxidation product such that the flow of said inerts passing into the reactor is substantially reduced.

20 Claims, No Drawings

OXYGEN ADDITION TO REDUCE INERTS IN AN ACRYLONITRILE REACTOR

FIELD OF THE INVENTION

A process for increasing the yield of an ammoxidation product. More particularly, the present invention is directed to a process for adding oxygen to reduce inerts in an acrylonitrile reactor without increasing the air flow such that the yield of an ammoxidation product is increased.

BACKGROUND OF THE INVENTION

The production of nitrites by ammoxidation of an appropriate alkene in the presence of a suitable catalyst is well known. The production of acrylonitrile from a gaseous feed of propylene, ammonia and air is described by Bruce E. Gates et al., in Chemistry of Catalytic Processes, McGraw-Hill (1979), pp.380–384.

The feed is sent to an ammoxidation reactor where, in the presence of a suitable catalyst, acrylonitrile is produced along with lesser amounts of other nitrogen-containing compounds. The effluent from the ammoxidation reaction is first quenched and then contacted countercurrently with water in an absorption tower. The desired products are recovered from the absorber in the aqueous phase. The absorbed off gas, typically oxygen, carbon dioxide, carbon monoxide, nitrogen and unreacted hydrocarbon are combined with natural gas and sent to a boiler for combustion. See, U.S. Pat. Nos. 3,591,620 and 4,335,056.

The unreacted feed material may be recovered. For example, U.S. Pat. Nos. 4,849,537, 4,870,201 and 5,015,756 teach the use of pressure swing adsorption type separators to recover unreacted propylene in an acrylonitrile process. The use of oxygen enriched air is generally coupled with a pressure swing adsorption separator.

U.S. Pat. No. 5,466,857 relates to reducing the amount of unreacted ammonia during the ammoxidation process by adding an additional amount of oxygen to the lower portion of a fluidized bed so that the oxygen can react with the unreacted ammonia. U.S. Pat. No. 5,457,223 relates to reducing ammonia breakthrough during the ammoxidation process by adding an additional amount of oxygen to the upper portion of a fluidized bed to react with unreacted ammonia.

Japanese Application No. 55[1980]-83,452 relates to a single source of oxygen which is split into two streams in which one of the streams is premixed with ammonia and the hydrocarbon reactant.

The art does not address or remedy the undesirable but important aspect of the presence of inerts in the ammoxidation process. "Inerts" in the general sense is defined herein as chemical species that are substantially non-reactive at the conditions at which the ammoxidation take place. In air based ammoxidation, the primary inert is nitrogen. As the presence of inerts in the ammoxidation process corresponds to a decrease in acrylonitrile yield, removing or decreasing the inerts is believed to increase the yield of the final acrylonitrile yield of the ammoxidation reaction therefrom.

OBJECTS OF THE INVENTION

It is therefore an object of the invention to provide an ammoxidation process which will result in a reduced amount of inerts.

It is a further object to reduce the amount of catalyst lost from the reactor in the ammoxidation process.

It is still another object to increase the amount of ammonia reacted in the ammoxidation process, which reduces the amount of unreacted ammonia effluent from the reactor.

It is still yet another object to reduce the energy requirement of the ammoxidation process.

SUMMARY OF THE INVENTION

This invention provides a process for increasing the yield of an ammoxidation product comprising the steps of passing an ammonia and a hydrocarbon stream into a catalyzed fluidized bed reactor; passing an oxygen-containing gas stream containing at least a portion of inerts into the reactor, passing a substantially pure oxygen stream into the reactor, and reducing the flow of the oxygen-containing gas stream while increasing the flow of the substantially pure oxygen stream, wherein the total rate of flow of oxygen from the oxygen-containing gas stream and the substantially pure oxygen stream is maintained in an effective amount to produce the ammoxidation product such that the flow of the inerts passing into the reactor is substantially reduced.

In a preferred embodiment, the ammonia and hydrocarbon streams passing into the reactor are combined into one stream prior to passing into the reactor. The oxygen content of the oxygen-containing gas may be that of air, about 21%, or may be greater than about 21% after removing at least a portion of inerts. The substantially pure oxygen has an oxygen purity content of greater than about 95%. Also, the substantially pure oxygen stream may be premixed with the ammonia and hydrocarbon streams prior to passing into the reactor.

DETAILED DESCRIPTION OF THE PREFERRED EMBODIMENT

While the invention will hereinafter be described in the context of fluidized bed acrylonitrile production process, those skilled in the art will realize that it is equally applicable to other processes which entrain an oxygen-containing gas with a reactant stream feed to a fluidized bed reactor.

The present invention provides an ammoxidation process which results in a reduced amount of inerts as compared to the conventional process. The amount of catalyst lost is also reduced. This process enables a greater amount of ammonia to react such that the amount of ammonia effluent from the reactor is reduced. Overall, the present invention enables the ammoxidation process to proceed with a lower energy requirement than that of the process in the art.

This invention provides a process for increasing the yield of an ammoxidation product comprising the steps of passing an ammonia and a hydrocarbon stream into a catalyzed fluidized bed reactor; passing an oxygen-containing gas stream containing at least a portion of inerts into the reactor, passing a substantially pure oxygen stream into the reactor, and reducing the flow of the oxygen-containing gas stream while increasing the flow of the substantially pure oxygen stream, wherein the total rate of flow of oxygen from the oxygen-containing gas stream and the substantially pure oxygen stream is maintained in an effective amount to produce the ammoxidation product such that the flow of the inerts passing into the reactor is substantially reduced.

In another embodiment, this invention is directed to a process for increasing the yield of an ammoxidation product comprising the steps of passing an ammonia and hydrocarbon stream into a catalyzed fluidized bed reactor, passing an oxygen-containing gas stream containing at least a portion of inerts into the reactor, the oxygen-containing gas stream having been produced by removing at least one portion of the inerts, wherein the rate of flow of oxygen from the oxygen-containing gas stream is maintained in an effective amount to produce the ammoxidation product such that the flow of the inerts passing into the reactor is substantially reduced.

In yet another embodiment, this invention is directed to a process for increasing the yield of an ammoxidation product comprising the steps of passing an ammonia and a hydrocarbon stream into a catalyzed fluidized bed reactor, passing an oxygen-containing gas stream containing at least a portion of inerts into the reactor, and passing a substantially pure oxygen stream into the reactor, wherein the total rate of flow of oxygen from the oxygen-containing gas stream and the substantially pure oxygen stream is maintained in an effective amount to produce the ammoxidation product such that the flow of the inerts to the reactor is substantially reduced.

In the process of this invention, the ammonia and hydrocarbon streams passing into the reactor may be separate streams or combined into one stream prior to passing into the reactor. The oxygen content of the oxygen-containing gas is that of air, about 21%, or greater than about 21% after removing at least a portion of inerts. The substantially pure oxygen has an oxygen purity content of greater than about 95%. Also, the substantially pure oxygen stream may be premixed with the ammonia and hydrocarbon streams prior to passing into the reactor.

Acrylonitrile is made via an air based ammoxidation of propylene in a fluidized bed reactor. Generally, air is routed to the base of the catalyst bed and is used to fluidize the catalyst. Ammonia and propylene are mixed together at a nearly one-to-one molar ratio and injected into the bed at some location above the air inlet. The propylene conversion is near 100% and the yield of the acrylonitrile produced is approximately 75%. The reactor effluent (primarily unreacted ammonia, propylene, oxygen, nitrogen, acrylonitrile, hydrogen cyanide and carbon oxides) is subsequently quenched with water. The acrylonitrile product, and sometimes byproduct hydrogen cyanide and acetonitrile are recovered through a series of distillation columns. The vent gas is sent to a boiler where it is combusted. The liquid waste (primarily aqueous ammonium sulfate which is the form in which the unreacted ammonia is recovered) is typically disposed of in some manner such as deep well injection.

All other things being equal, when the pressure in an acrylonitrile reactor is decreased, the yield of an acrylonitrile is increased. For every pound per square inch (psi) that the pressure is reduced, it is estimated that the acrylonitrile yield increases by about 0.2% yield points (absolute). As a result, if the pressure decreases in a conventional reactor, the yield will similarly decrease.

One method to reduce pressure in the reactor is to reduce the flow of gas to the reactor. In a conventional reactor, the flow of gas can only be reduced in a limited number of ways: 1) Reduced air flow. Reduction of air flow will reduce the yield. As oxygen is a component in air, the reduction in air flow will correspondingly reduce oxygen in the reactor effluent. The percentage of oxygen must be maintained at or above a certain percentage in order to maintain an acrylonitrile yield and catalyst activity. Typically, the lowest possible oxygen concentration is used in order to maximize throughput, which is the amount of propylene processed in the reactor, i.e., production. If the air flow is reduced, the oxygen percentage in the effluent will be lowered below the critical value, thereby reducing the yield and also rendering the catalyst useless. 2) Reduce feed flow. If the feed flow is reduced, the production will necessarily be reduced because fewer reactant molecules will enter the reactor. The yield gain (the greater fraction of the reactant molecules transformed into product molecules) is generally insufficient to make up for the feed reduction. 3) Reduce both air and feed flow. Similarly, a reduction in feed flow will reduce the production of the acrylonitrile, as the yield gain is not enough to make up for the feed reduction.

The present invention differs from the conventional air enrichment because the present invention reduces the amount of inerts to the reactor while maintaining a constant ammonia-propylene feed rate. When this is done, the oxygen percentage in the reactor effluent can be maintained with a significantly reduced air flow. When the air flow is reduced, the pressure in the reactor is also reduced. Thus, adding oxygen in this manner leads to an increase in acrylonitrile yield based on the pressure-yield relationship without sacrificing production or lowering the oxygen percentage in the effluent. Furthermore, the total reduction in gas flow will reduce the amount of catalyst that is lost through being blown out of the reactor or wasted in an unused condition.

Some other benefits of this invention may be realized as follows. These include the reduction of the amount of catalyst loss that is being blown into the downstream unit operations. This lost catalyst may cause damage to the operation of the downstream pieces of equipment and must also be disposed of as a hazardous waste. The reduction in catalyst loss also lowers maintenance costs as well as hazardous waste removal costs.

Increasing the acrylonitrile yield increases the amount of ammonia which is reacted. This reduces the amount of ammonia that exits the reactor. The unreacted ammonia is neutralized with sulfuric acid and then typically deep welled. When the ammonia break through is reduced, the amount of sulfuric acid needed and liquid waste formed is also reduced.

The reduction in air flow reduces the amount of inerts in the vent gas since the amount of nitrogen is reduced. This increases the heating value of the vent gas. Thus, a lower amount of natural gas than usually required in the art is needed to burn the vent gas.

It is also known that reduction in air flow reduces the energy requirement of the air compressor. As a result, significant cost savings associated with energy consumption in reducing air flow.

The yield increase, reduction in catalyst loss, and associated benefits all produce cost savings without sacrificing the production of acrylonitrile. These savings are a significant economic advantage over both conventional reactor operation and conventional reactor operation and conventional air enrichment.

Additionally, the physical changes made to the process so that oxygen can be added to the reactor as described in this invention also allow oxygen to be added in the conventional manner (without reducing air flow) to increase production. Thus, in times of high demand for acrylonitrile, oxygen can be used to increase production, but in times of low demand, it can be used to reduce cost. If constant addition of oxygen is used, the acrylonitrile producer can ensure agreeable pricing by purchasing oxygen in volume so as to effect a good agreeable price.

As provided in this invention, there are at least two preferred embodiments for practicing this invention: adding oxygen to the feed stream (direct injection) and adding oxygen to the air stream.

Generally, greater yield can usually be achieved by adding oxygen to the feed stream because it adds oxygen into an oxygen deficient area of the reactor. The effectiveness of direct injection depends on the available catalyst and reactor design. The advantages and optimum practices are described in commonly assigned and copending U.S. patent application Ser. No. 08/519,011 filed Aug. 24, 1995 and Ser. No.

08/823,701 filed Mar. 25, 1997, which is a continuation application of U.S. application Ser. No. 08/519,003 filed Aug. 24, 1995, now abandoned, which are incorporated herein by reference.

Direct injection is exemplified by providing an oxygen-bearing gas and a gaseous reactant stream to a fluidized bed reactor. A sparger causes an entraining of the oxygen-bearing gas into the reactant gas stream. A feed line couples the sparger to the reactor's fluidized bed and introduces the reactant gas stream and entrained oxygen-bearing gas directly into contact with the fluidized bed. A controller controls both the amount of oxygen-bearing gas and the gaseous reactant so that, at the point of feed injection, the fluidized bed catalyst does not experience an oxygen deficiency. To assure safety, the reactant content of the combined feed and oxygen stream is maintained above an upper flammability limit, preferably with a safety margin of at least 10%.

A second method for injecting oxygen is by adding the oxygen to the air stream. This method enables more oxygen to be injected than the direct injection method. In this sense, adding oxygen to the air stream may produce greater yield if the direct injection method as mentioned above is not effective. Injecting a greater amount of oxygen enables a greater production increase if the oxygen is injected without reducing the air flow. The equipment required to do this is also less complicated and less expensive than that required for direct injection. Typically, the oxygen will be added to the air stream to make the air-oxygen stream 25% oxygen.

The choice between adding the oxygen to the feed stream as a direct injection or adding the oxygen to the air stream will depend on the effectiveness of the direct injection and on whether the additional capability to increase production by a large amount is desired. If producing a large portion is contemplated, then it is preferable to add the oxygen to the air stream. However, if increased yield is contemplated, then it is preferable to add oxygen to the air feed as direct injection.

Although adding oxygen to either the air stream or the feed stream is the more preferred method, other methods are also available. For example, oxygen may be added directly to the reactor. In another embodiment, oxygen may be added to both the feed and the air stream. In yet another embodiment, oxygen may be added to the reactor, the feed stream as well as to the air stream.

In addition to the use of air, and of substantially pure oxygen, this invention also contemplates the use of oxygen-enriched air. As used herein, substantially pure oxygen has an oxygen content of greater than about 95%. The oxygen-enriched air has an oxygen content of greater than about 21%, and preferably an oxygen content of between about 21% to about 30%.

Further alternative embodiments will be recognized by those skilled in the art and are intended to be included within the scope of the claims.

What is claimed is:

1. A process for increasing the yield of an ammoxidation product comprising
   a) passing an ammonia and a hydrocarbon stream into a catalyzed fluidized bed reactor,
   b) passing an oxygen-containing gas stream containing at least a portion of inerts into said reactor,
   c) passing a substantially pure oxygen stream into said reactor, and
   d) reducing the flow of said oxygen-containing gas stream to reduce the flow of said inerts passing into said reactor while increasing the flow of said substantially pure oxygen stream,
   wherein the total rate of flow of oxygen from said oxygen-containing gas stream and said substantially pure oxygen stream is maintained in an effective amount to produce the ammoxidation product.

2. The process of claim 1 wherein said ammonia and hydrocarbon streams passing into said reactor are separate streams.

3. The process of claim 1 wherein said ammonia and hydrocarbon streams are combined prior to passing into said reactor.

4. The process of claim 1 wherein said substantially pure oxygen has an oxygen purity content of greater than about 95%.

5. The process of claim 1 wherein said substantially pure oxygen stream is premixed with said ammonia and hydrocarbon streams prior to passing into said reactor.

6. A process for increasing the yield of an ammoxidation product comprising
   a) passing an ammonia and hydrocarbon stream into a catalyzed fluidized bed reactor, and
   b) passing an oxygen-containing gas stream containing at least a portion of inerts into said reactor, said oxygen-containing gas stream having been produced by removing at least one portion of said inerts,
   wherein the rate of flow of oxygen from said oxygen-containing gas stream is maintained in an effective amount to produce said ammoxidation product such that the flow of said inerts passing into said reactor is substantially reduced.

7. The process of claim 6 wherein said ammonia and hydrocarbon streams are combined prior to passing into said reactor.

8. The process of claim 6 wherein said oxygen-containing gas after removing at least a portion of inerts has an oxygen content of greater than about 21%.

9. The process of claim 6 wherein said ammonia and hydrocarbon streams passing into said reactor are separate streams.

10. The process of claim 9 wherein said substantially pure oxygen stream is premixed with said ammonia and hydrocarbon streams prior to passing into said reactor.

11. The process of claim 9 wherein said ammonia and hydrocarbon streams are combined prior to passing into said reactor.

12. The process of claim 9 wherein said oxygen-containing gas after removing at least said portion of inerts has an oxygen content of greater than about 21%.

13. A process for increasing the yield of an ammoxidation product comprising
   a) passing an ammonia and a hydrocarbon stream into a catalyzed fluidized bed reactor,
   b) passing an oxygen-containing gas stream containing at least a portion of inerts into said reactor, and
   c) passing a substantially pure oxygen stream into said reactor,
   wherein the total rate of flow of oxygen from said oxygen-containing gas stream to reduce the flow of said inerts passing into said reactor and said substantially pure oxygen stream is maintained in an effective amount to produce said ammoxidation product.

14. The process of claim 13 wherein said substantially pure oxygen stream is premixed with said ammonia and hydrocarbon streams prior to passing into said reactor.

15. The process of claim 13 wherein said substantially pure oxygen has an oxygen purity content of greater than about 95%.

16. The process of claim 13 wherein said oxygen-containing gas after removing at least said portion of inerts has an oxygen content of greater than about 21%.

17. The process of claim 13 wherein said substantially pure oxygen stream is premixed with said ammonia and hydrocarbon streams prior to passing into said reactor.

18. The process of claim 13 wherein said ammonia and hydrocarbon streams passing into said reactor are separate streams.

19. The process of claim 18 wherein said ammonia and hydrocarbon streams are combined prior to passing into said reactor.

20. The process of claim 18 wherein said oxygen-containing gas after removing at least said portion of inerts has an oxygen content of greater than about 21%.

* * * * *